US012694479B2

(12) United States Patent
Bagherinia et al.

(10) Patent No.: US 12,694,479 B2
(45) Date of Patent: Jul. 28, 2026

(54) SYSTEM AND METHOD OF A PROCESS FOR ROBUST MACULAR THICKNESS ANALYSIS USING LOW-COST LINE-FIELD OPTICAL COHERENCE TOMOGRAPHY (OCT)

(71) Applicant: CARL ZEISS MEDITEC, INC., Dublin, CA (US)

(72) Inventors: Homayoun Bagherinia, Oakland, CA (US); Conor Leahy, Dublin, CA (US); Simon Bello, Walnut Creek, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 551 days.

(21) Appl. No.: 18/081,857

(22) Filed: Dec. 15, 2022

(65) Prior Publication Data

US 2023/0196532 A1 Jun. 22, 2023

Related U.S. Application Data

(60) Provisional application No. 63/290,548, filed on Dec. 16, 2021.

(51) Int. Cl.
| | |
|---|---|
| *G06T 5/50* | (2006.01) |
| *A61B 3/10* | (2006.01) |

(Continued)

(52) U.S. Cl.
CPC ............. *G06T 5/50* (2013.01); *A61B 3/1005* (2013.01); *A61B 3/102* (2013.01); *A61B 3/12* (2013.01);

(Continued)

(58) Field of Classification Search
CPC ......... A61B 3/102; A61B 3/1005; A61B 3/12; A61B 3/0025; A61B 5/0022;

(Continued)

(56) References Cited

U.S. PATENT DOCUMENTS

| | | | |
|---|---|---|---|
| 6,549,801 | B1 | 4/2003 | Chen et al. |
| 6,741,359 | B2 | 5/2004 | Wei et al. |

(Continued)

FOREIGN PATENT DOCUMENTS

| | | | |
|---|---|---|---|
| JP | 2018143435 A | * | 9/2018 |
| WO | 2012059236 | | 5/2012 |

(Continued)

OTHER PUBLICATIONS

Lang, A. et al. "Combined registration and motion correction of longitudinal retinal OCT data," Proc SPIE Int Soc Opt Eng. Feb. 27, 2016; 9784. doi:10.1117/12.2217157.

(Continued)

*Primary Examiner* — Sumati Lefkowitz
*Assistant Examiner* — Anna Lei
(74) *Attorney, Agent, or Firm* — SNELL & WILMER L.L.P.

(57) ABSTRACT

A system and method for creating a composite retinal thickness map of an eye, including collecting, by an optical coherence tomography (OCT) device, a set of a plurality of optical coherence tomography (OCT) volume scans of the eye. At least one set of the plurality of OCT volume scans is collected by the OCT device.

16 Claims, 12 Drawing Sheets
(6 of 12 Drawing Sheet(s) Filed in Color)

(51) Int. Cl.

| | |
|---|---|
| *A61B 3/12* | (2006.01) |
| *A61B 5/00* | (2006.01) |
| *G06T 5/77* | (2024.01) |
| *G06T 7/00* | (2017.01) |
| *G06T 7/174* | (2017.01) |
| *G06T 7/33* | (2017.01) |

(52) U.S. Cl.
CPC .............. *A61B 5/0022* (2013.01); *G06T 5/77* (2024.01); *G06T 7/0014* (2013.01); *G06T 7/174* (2017.01); *G06T 7/337* (2017.01); *G06T 2207/10101* (2013.01); *G06T 2207/20216* (2013.01); *G06T 2207/30041* (2013.01)

(58) Field of Classification Search
CPC . G06T 2207/10101; G06T 2207/30041; G06T 5/50; G06T 7/0014; G06T 7/174; G06T 7/337; G06T 2207/20216; G06T 7/10
See application file for complete search history.

(56) References Cited

U.S. PATENT DOCUMENTS

| | | | |
|---|---|---|---|
| 7,301,644 | B2 | 11/2007 | Knighton et al. |
| 7,359,062 | B2 | 4/2008 | Chen et al. |
| 7,997,728 | B2 * | 8/2011 | Huang ................... A61B 3/102 |
| | | | 351/200 |
| 8,223,143 | B2 * | 7/2012 | Dastmalchi ............. G06T 19/00 |
| | | | 345/418 |
| 8,433,393 | B2 | 4/2013 | Sharma et al. |
| 8,868,155 | B2 * | 10/2014 | Debuc ................... G06T 7/0014 |
| | | | 600/407 |
| 8,967,806 | B2 | 3/2015 | Bublitz et al. |
| 8,998,411 | B2 | 4/2015 | Tumlinson et al. |
| 9,456,746 | B2 | 10/2016 | Bublitz et al. |
| 9,700,206 | B2 | 7/2017 | An et al. |
| 9,706,915 | B2 | 7/2017 | Everett et al. |
| 9,759,544 | B2 | 9/2017 | An et al. |
| 9,778,021 | B2 | 10/2017 | Bagherinia et al. |
| 10,094,649 | B2 | 10/2018 | Bagherinia et al. |
| 2008/0100612 | A1 * | 5/2008 | Dastmalchi ............ A61B 3/102 |
| | | | 345/418 |
| 2010/0027857 | A1 | 2/2010 | Wang |
| 2012/0307014 | A1 | 12/2012 | Wang |
| 2015/0131050 | A1 | 5/2015 | Bublitz et al. |
| 2020/0288971 | A1 * | 9/2020 | Huang ................... G06T 7/168 |
| 2021/0235984 | A1 * | 8/2021 | Scheibler ............. A61B 3/0008 |
| 2021/0401286 | A1 * | 12/2021 | Walsh .................... A61B 3/085 |
| 2022/0092780 | A1 * | 3/2022 | Chauhan .............. G06T 7/0012 |
| 2022/0319070 | A1 * | 10/2022 | Pellegrini ............ G06V 40/193 |

FOREIGN PATENT DOCUMENTS

| | | |
|---|---|---|
| WO | 2015013050 | 1/2015 |
| WO | 2016124644 | 8/2016 |

OTHER PUBLICATIONS

Kepp, T. et al. "Segmentation of retinal low-cost optical coherence tomography images using deep learning," SPIE Medical Imaging, vol. 11314. p. 1131410, 2020, Houston, Texas. International Society for Optics and Photonics. SPIEDigitalLibrary.org/conference-proceedings-of-spie. Accessed Mar. 15, 2023.

Barnum, P. et al. "Local Quality Assessment for Optical Coherence Tomography," Robotics Institute Intel Research Pittsburgh UPMC Eye Center, Department of Ophthalmology Carnegie Mellon, University of Pittsburgh School of Medicine. 2008 5th IEEE International Symposium on Biomedical Imaging.

Wu, J. et al. "Stable Registration of Pathological 3D SD-OCT Scans using Retinal Vessels," Ophthalmic Medical Image Analysis First International Workshop, OMIA 2014, Held in Conjunction with MICCAI Sep. 2014.

* cited by examiner

300

310        320

400

410        420        430

440        450        460

1410

Layr1: Inner Limiting Membrane (ILM)
Layr2: (Retinal) Nerve Fiber Layer (RNFL or NFL)
Layr3: Ganglion Cell Layer (GCL)
Layr4: Inner Plexiform Layer (IPL)
Layr5: Inner Nuclear Layer (INL)
Layr6: Outer Plexiform Layer (OPL)
Layr7: Outer Nuclear Layer (ONL)
Layr8: Junction between Outer Segments (OS) and Inner Segments (IS)
Layr9: Extertnal/Outer Limiting Membrane (ELM/OLM)
Layr10: Retinal Pigment Epithelium (RPE)
Layr11: Bruch's Membrance (BM)

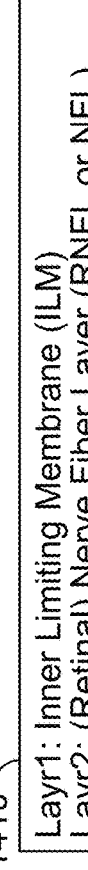

1420

Fovea

Choroid

Layr-8

Layr-9

Layr1
Layr2
Layr3
Layr4
Layr5
Layr6
Layr7
Layr10

Layr11

SYSTEM AND METHOD OF A PROCESS FOR ROBUST MACULAR THICKNESS ANALYSIS USING LOW-COST LINE-FIELD OPTICAL COHERENCE TOMOGRAPHY (OCT)

CROSS-REFERENCE TO RELATED APPLICATIONS

This application claims the benefit of priority under 35 U.S.C. 120 to U.S. Provisional Application Ser. No. 63/290, 548 entitled "STRATEGY FOR ROBUST MACULAR THICKNESS ANALYSIS USING LOW-COST LINE-FIELD OCT", filed on Dec. 16, 2021, the entire contents of which are incorporated by reference for all purposes.

FIELD OF INVENTION

The present invention is generally directed to remote Optical Coherence Tomography (OCT) systems. More specifically, it is directed to techniques of data analyses of low-quality OCT data to determine or assess macular thickness data.

BACKGROUND

Optical coherence tomography (OCT) is a non-invasive imaging technique that uses light waves to penetrate tissue and produce image information at different depths within the tissue, such as an eye. Generally, an OCT system is an interferometric imaging system based on detecting the interference of a reference beam and backscattered light from a sample illuminated by an OCT beam. Each scattering profile in the depth direction (e.g., z-axis or axial direction) may be reconstructed individually into an axial scan, or A-scan. Cross-sectional slice images (e.g., two-dimensional (2D) bifurcating scans, or B-scans) and volume images (e.g., 3D cube scans, or C-scans) may be built up from multiple A-scans acquired as the OCT beam is scanned/moved through a set of transverse (e.g., x-axis and/or y-axis) locations on the sample. When applied to the retina of an eye, OCT generally provides structural data that, for example, permits one to view, at least in part, distinctive tissue layers and vascular structures of the retina. OCT angiography (OCTA) expands the functionality of an OCT system to also identify (e.g., render in image format) the presence, or lack, of blood flow in retinal tissue. For example, OCTA may identify blood flow by identifying differences over time (e.g., contrast differences) in multiple OCT scans of the same retinal region, and designating differences in the scans that meet predefined criteria as blood flow.

An OCT system also permits the construction of a planar (2D), frontal view (e.g., en face) image of a select portion of a tissue volume (e.g., a target tissue slab (sub-volume) or target tissue layer(s), such as the retina of an eye). Examples of other 2D representations (e.g., 2D maps) of ophthalmic data provided by an OCT system may include layer thickness maps and retinal curvature maps. For example, to generate layer thickness maps, an OCT system may use en-face images, 2D vasculature maps of the retina, and multilayer segmentation data. Thickness maps may be based, at least in part, on measured thickness differences between retinal layer boundaries. Vasculature maps and OCT en face images may be generated, for example, by projecting onto a 2D surface a sub-volume (e.g., tissue slab) defined between two layer boundaries. The projection may use the sub-volume mean, sum, percentile, or other data aggregation methods. Thus, the creation of these 2D representations of 3D volume (or sub-volume) data often relies on the effectiveness of automated segmentation algorithms to identify the layers upon which the 2D representations are based.

2-D representation of 3-D OCT volume is one of the OCT visualization approaches that has significantly benefited from technical advancements in OCT technology. One example of a 2-D representation of 3-D OCT volume is a macular thickness map. The macular thickness is typically measured based on the difference between the inner limiting membrane (ILM) and the retinal pigment epithelium (RPE) layer boundaries.

Typically, a patient visits a doctor's office (or clinic) to have an OCT scan administered by a trained technician. When monitoring a patient's eye for a disease, however, frequent and/or regular OCT scans are generally needed to identify the early onset of the disease or early diagnosis of disease progression. Frequent doctor visits can be a burden for a patient, particularly for the elderly. A home-use (or remote) OCT system/device that would permit a patient to self-administer an OCT scan would be helpful in mitigating the need for frequent doctor visits.

A drawback with home-use OCT systems is that whereas professional-grade OCT systems, such as those typically found in doctor's offices, are generally large, expensive, and provide high-quality data; remote and home-use OCT systems tend to be low-cost and provide low-quality images. These low-quality images generally make it difficult to apply the necessary data analysis to diagnose disease onset and/or progression.

It is an object of the present invention to provide a system/method for enhanced and consistent extraction of macular thickness map data from low-quality images, such as those produced by home-use (or remote) OCT systems/devices.

SUMMARY

In an exemplary embodiment, a method of creating a composite retinal thickness map of an eye is provided. The method includes collecting, by an optical coherence tomography (OCT) device, a set of a plurality of optical coherence tomography (OCT) volume scans of the eye, wherein at least one set of the plurality of OCT volume scans are collected by the OCT device by segmenting a target upper retinal layer and a target lower retinal layer which is lower than the target upper retinal layer within an OCT volume scan; determining a thickness map of a candidate between the upper retinal layer and lower retinal layer, and a confidence map associated with the thickness map; selecting at least one thickness map as a reference thickness map; registering at least one thickness map to the reference thickness map; and selectively combining a region of the thickness map with a corresponding region of the reference thickness map to define a composite retinal thickness map.

In various exemplary embodiments, selectively combining the region of the thickness map with a corresponding region of the reference thickness map includes identifying the region of low quality within the reference thickness map based on the confidence map; and replacing the region of low quality with a combination of the corresponding region from an alternate thickness map.

In various exemplary embodiments, the corresponding region is of higher quality than a low-quality region based on the confidence map.

In various exemplary embodiments, the selected reference thickness map is the thickness map that has the highest confidence measure based on the confidence map.

In various exemplary embodiments, the confidence map is based on at least one of the corresponding OCT signal quality maps and segmentation confidence map.

In various exemplary embodiments, the region that is selected from the thickness map is combined with the corresponding region of the reference thickness map using a weighted average function.

In various exemplary embodiments, the weighted average function is based at least on the confidence map of the selected region of a thickness map.

In various exemplary embodiments, the target upper retinal layer is an internal limiting membrane (ILM) layer, and the target lower retinal layer is lower than a retinal pigment epithelium (RPE) layer.

In various exemplary embodiments, at least one set of the plurality of volume scans is associated with a corresponding segmentation confidence map wherein at least one thickness map is registered to the reference thickness map wherein registration includes transforming the corresponding segmentation confidence map based on at least one thickness map.

In various exemplary embodiments, the selection of a corresponding region from the other candidate thickness maps is enabled by the combination of a weighted average of at least one individual registered map wherein a set of weights for a weighted average is based on a corresponding confidence map.

In various exemplary embodiments, at least one region of the candidate thickness map is selected for processing with information associated with an Early Treatment Diabetic Retinopathy Study (ETDRS).

In various exemplary embodiments, a remote self-examination system for creating a composite retinal thickness map of an eye is provided. The system includes an optical coherence tomography (OCT) device for collecting a set of a plurality of OCT volume scans of the eye; a computing device disposed of in the OCT device to process data of at least one set of the plurality of OCT volume scans wherein the computing device is configured to segment a target upper retinal layer and a target lower retinal layer lower than the target upper retinal layer within an OCT volume scan; determine a thickness map of a candidate between the upper retinal layer and lower retinal layer, and a confidence map associated with the thickness map; select at least one thickness map as a reference thickness map; register the thickness map to the reference thickness map; and selectively combine a region of the thickness map with a corresponding region of the reference thickness map to define a composite retinal thickness map.

In various exemplary embodiments, the OCT device further comprises an electronic communication module to transmit a report based on the defined composite retinal thickness map to a remote health care center.

In various exemplary embodiments, the computing device is further configured to: selectively combine the region of the thickness map with the corresponding region of the reference thickness map by identifying regions of low quality within the reference thickness map associated with the confidence map; and replacing the identified regions of low quality with a combination of a selected corresponding region from an alternate thickness map.

In various exemplary embodiments, the computing device is further configured to select a corresponding region that is of higher quality than a low-quality region based on an association of the confidence map to the corresponding region.

In various exemplary embodiments, the computing device is further configured to select the reference thickness map that includes the thickness map having the highest confidence measure based associated with the confidence map.

In various exemplary embodiments, the confidence map is based on at least one corresponding OCT signal quality map and a segmentation confidence map.

In various exemplary embodiments, the region from the thickness map is combined with the corresponding region of the reference thickness map by a weighted average.

In various exemplary embodiments, the computing device is configured to apply a weighted average function based at least on the confidence map of a selected region of the thickness map.

In various exemplary embodiments, the target upper retinal layer is an internal limiting membrane (ILM) layer, and the target lower retinal layer is lower than a retinal pigment epithelium (RPE) layer.

In various exemplary embodiments, at least one set of the volume scans that have been collected is associated with a corresponding segmentation confidence map, wherein the register of the thickness map to the reference thickness map comprises the transformation of a segment of the confidence map to a corresponding thickness map.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIG. 14 illustrates an exemplary diagram that shows an exemplary OCT B-scan image of a normal retina of a human eye and illustratively identifies various canonical retinal layers and boundaries in accordance with the present invention.

DESCRIPTION OF THE PREFERRED EMBODIMENTS

Figures 1, 2:
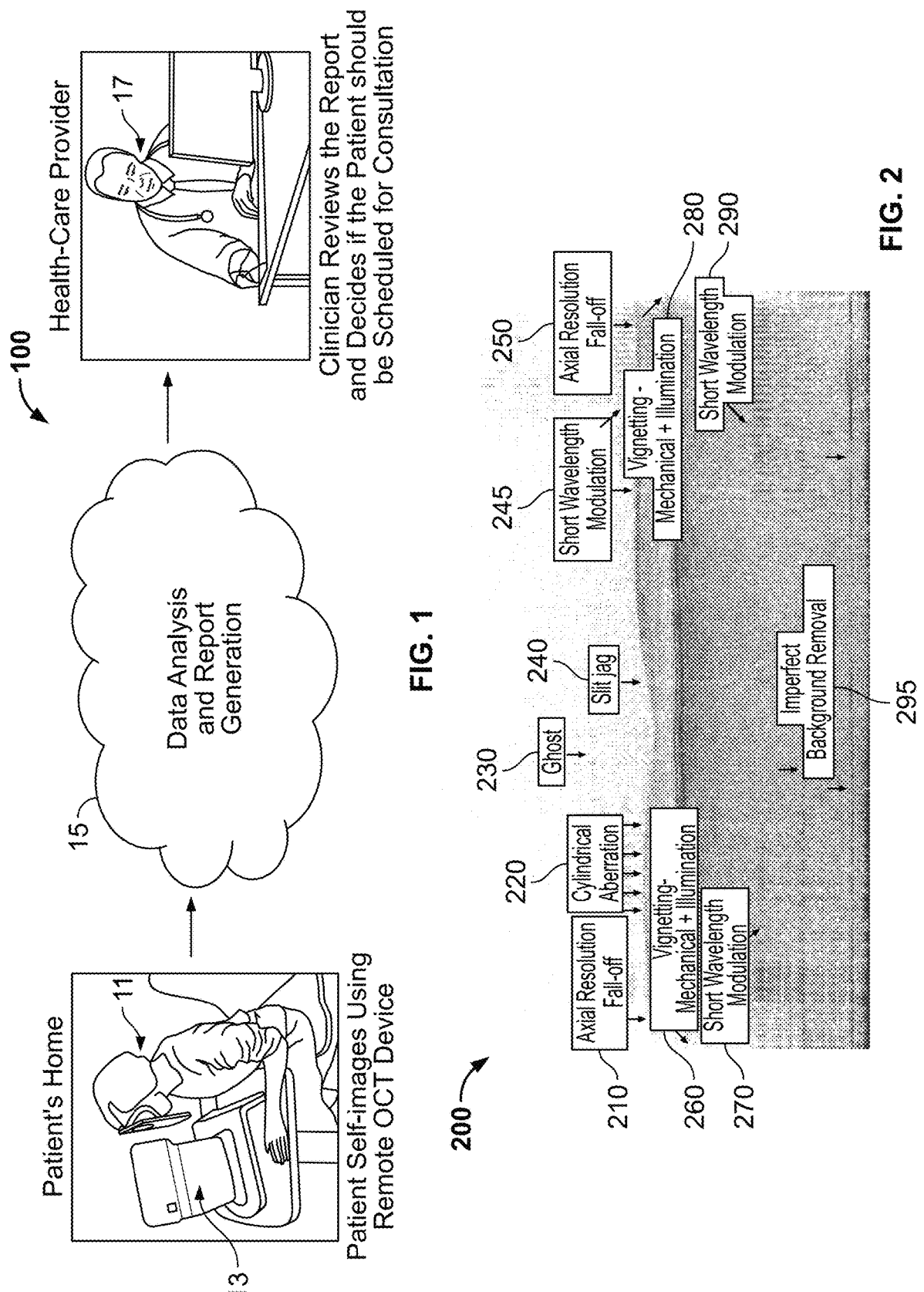
FIG. 1 illustrates an exemplary diagram of a workflow of a remote OCT device usage in accordance with the present invention.
FIG. 2 illustrates an exemplary diagram of some of the different impacts (manifestations) of these, and other, artifacts on a B-scan, as labeled in accordance with the present invention.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not for limitation. Furthermore, any reference to singular includes plural embodiments, and any reference to more than one component or step may include a singular embodiment or step. Also, any reference to attached, fixed, connected, or the like may include permanent, removable, temporary, partial, full, or any other possible attachment option. Additionally, any reference to without contact (or similar phrases) may also include reduced contact or minimal contact. It should also be understood that unless specifically stated otherwise, references to "a," "an" or "the" may include one or more than one, and that reference to an item in the singular may also include the item in the plural. Further, all ranges may include upper and lower values, and all ranges and ratio limits disclosed herein may be combined.

Remote OCT devices (e.g., personal-use or home-use or self-use or self-administered or self-applied OCT devices) may serve as a flagging/signaling/alerting mechanism to identify significant changes in retinal anatomy or physiology that may require (e.g., immediate) medical attention by trained personnel (e.g., a physician). For example, the OCT device may issue a (locally and/or remote) signal (e.g., electronic, audio, visual, haptic, etc.) alerting the patient and/or physician and/or clinic of the need for medical attention. The issued signal may also include an electronic message sent remotely to the patient's doctor (or doctor's office/clinic) by a telecommunication network (e.g., text message, electronic mail, internet, telephone, etc.). A goal of these systems is to allow for frequent self-monitoring of diagnosed ocular pathologies. To help this workflow to be successful, the OCT system should be able to provide accurate metrics and monitor their relative's changes over time. Macular thickness analysis is a well-established metric to quantify retinal changes. An increase in retinal thickness is frequently associated with the presence of intraretinal and subretinal fluid, which is a common reoccurring symptom of several ocular diseases and requires treatment.

In various exemplary embodiments, remote OCT applications are challenging because they generally require systems that are portable/small and cost-efficient (e.g., low cost) in order to promote the wide adoption of the technology. The cost constraints usually lead to the use of lower-end components that can compromise image quality, as well as the elimination of costly eye-tracking components. Therefore, there is a need for high-performing algorithms that can navigate data quality limitations (e.g., overcome lower quality OCT scan data, such as due to hardware constraints), and be able to quantify macular thickness changes over time.

In various exemplary embodiments, a method and system are provided that enable the registering of the thickness map to the reference thickness map comprising the transformation of the corresponding segmentation confidence map to a corresponding thickness map. In various exemplary embodiments, the method and system create a composite retinal thickness map of an eye, using a remote (e.g., homo-use), a low-cost OCT device that provides accurate macular thickness data. It does this by collecting/acquiring multiple optical coherence tomography (OCT) volume scans of an eye, and selectively combining usable (e.g., higher quality) scan data from the multiple OCT volume scans to produce a composite retinal thickness map that reliably and repeatedly generates accurate macular thickness data. To achieve this, for each of the collected volume scans, a target upper retinal layer and a target lower retinal layer is segmented. For example, the target upper retinal layer may be the internal limiting membrane (ILM) layer, and the target lower retinal layer lower may be the retinal pigment epithelium (RPE) layer. A candidate thickness map for each upper retinal layer and lower retinal layer is determined, and a confidence map associated with the determined candidate thickness map is likewise defined. To combine the multiple, thus determined thickness maps, one of the determined thickness maps is selected as a reference thickness map, and the remaining (other) determined thickness maps are registered to the selected reference thickness map. Regions of the registered candidate thickness maps are then selectively combined with corresponding regions of the reference thickness map to define the composite retinal thickness map.

Optionally, in various exemplary embodiments, a method or system is provided to selectively combine regions of the candidate thickness maps with corresponding regions of the reference thickness map may include steps of identifying regions of low quality within the reference thickness map based on its associated confidence map and replacing the identified regions of low quality with a combination of select corresponding regions from the other candidate thickness maps. In this case, the select corresponding regions may be selected for being of higher quality than the low-quality regions based on their respective confidence maps.

Preferably, the selected reference thickness map is the candidate thickness map having the highest confidence measure based on its associated confidence map. The confidence maps may be based on at least one corresponding OCT signal quality map and segmentation confidence map.

Optionally, in various exemplary embodiments, the method and system are provided to select regions from the candidate thickness maps and are combined with corresponding regions of the reference thickness map by a weighted average. The weighted average may be based at least in part on the confidence maps of the selected regions of the candidate thickness maps.

In an embodiment of the present invention, each of the collected volume scans has a corresponding segmentation confidence map, and the step of registering the determined thickness maps to the reference thickness map may include transforming the corresponding segmentation confidence map of each determined thickness map to its corresponding registered determined thickness map. In this case, select corresponding regions from the other candidate thickness maps may be combined by a weighted average of individual registered maps wherein the weights are based on their corresponding transformed segmentation confidence maps.

Optionally, in various exemplary embodiments, a method or system is provided in which the regions of the candidate thickness maps are selected for combining based on regions defined by information from an Early Treatment Diabetic Retinopathy Study (ETDRS).

Referring to FIG. 1, FIG. 1 illustrates diagram 100 of a process of remote OCT device usage in accordance with the present invention. A patient 11 self-images their eye(s) at home using a remote OCT device 13. The remote OCT device 13 generates and transmits a data analysis and report over a telecommunication network 15 to a clinician 17 for review, who may then schedule a medical consultation if needed.

In various embodiments, additional challenges related to remote applications of a remote OCT device (such as a low-cost, line-field (LF), Spectral Domain (SD) OCT device) include: No technician (trained operator) is present or available to administer the OCT scan and to evaluate the quality of the acquired/captured data; the remote OCT system must evaluate the captured data itself, and identify and re-acquire scans that are deemed to not be of sufficient quality for data analysis; the OCT system must maintain a high success rate since one of its purposes is to determine if the medical intervention (e.g., application of medication and/or a medical consultation) is required/warranted; and most captured OCT data will likely contain artifacts, which make the segmentation task challenging to perform with accuracy.

Referring to FIG. 2, there is illustrated various examples of different image artifacts commonly encountered in low-cost LF-SDOCT data including line artifacts (such as due to imperfect background subtraction), lost A-scans (such as due to saturation), and vignetting. In various embodiments, FIG. 2 illustrates in diagram 200 some of the different impacts (manifestations) of these, and other, artifacts on a B-scan, as labeled, and include axial resolution fall-out 210, cylindrical aberration 220, ghost 230, slit jag 240, short wavelength modulation 245, axial resolution fall-off 250 vignetting 260, short wavelength modulation 270, vignetting 280, short wavelength modulation 290 and imperfect background removal 295. In the present example, common artifacts are highlighted on a line-field spectral domain optical coherence tomography (LF-SDOCT) B-Scan.

Figure 3:
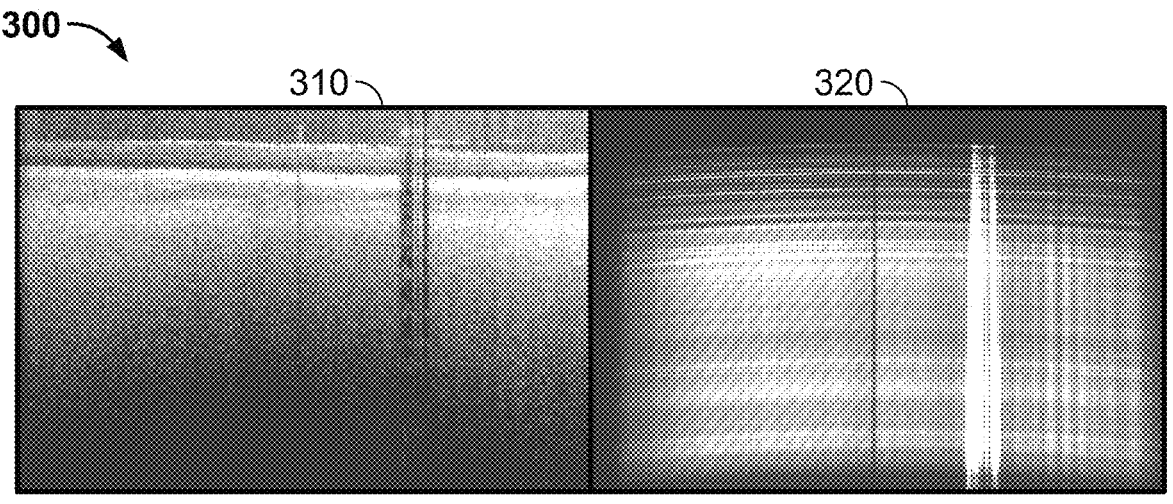
FIG. 3 illustrates exemplary A-scans that show loss of A-scans from a tomogram (left) due to sensor saturation in the raw interferogram (right), such as caused by a corneal reflex.

Furthermore, in various embodiments, bright reflections from the cornea and nerve fiber layer can lead to sensor saturation, resulting in partial loss of data from a B-scan. Referring to FIG. 3, FIG. 3 shows loss of A-scans 300 from a tomogram (left) 310 due to sensor saturation in the raw interferogram (right) 320, such as caused by a corneal reflex.

Figure 4:
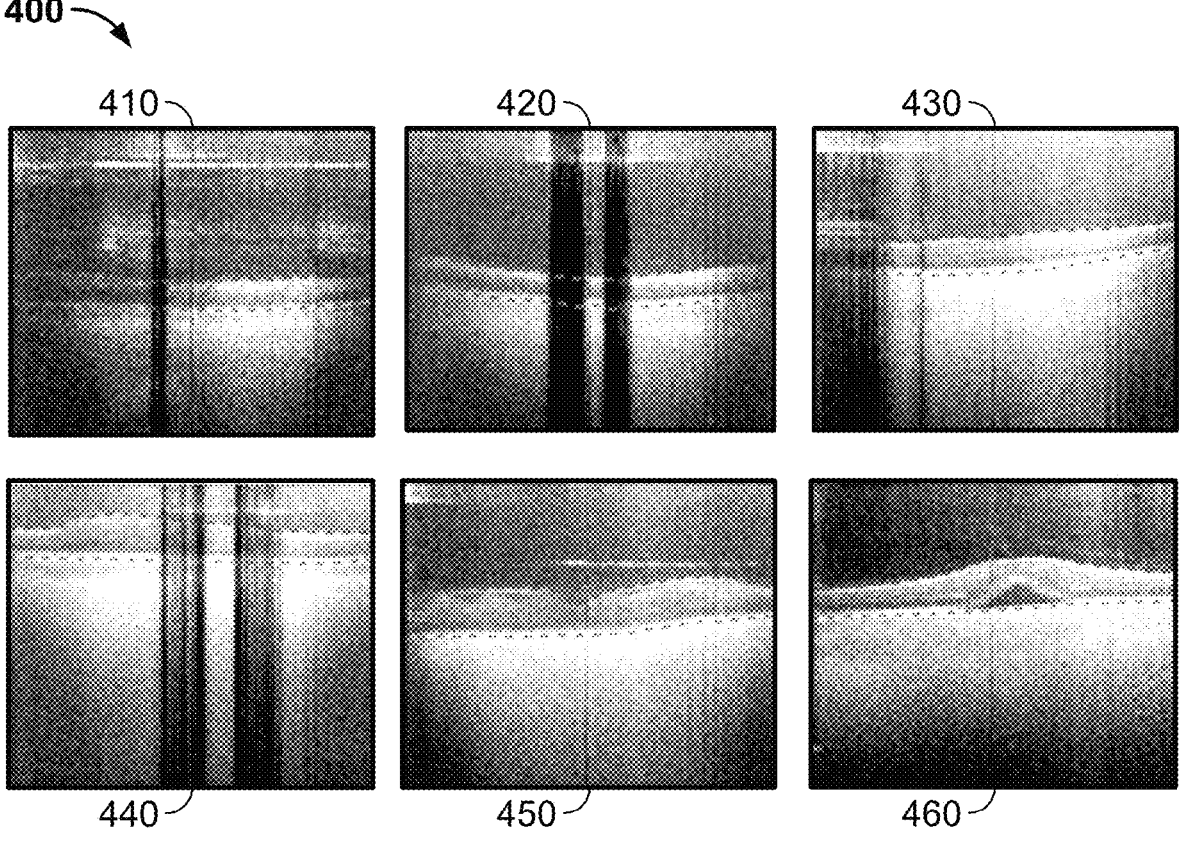
FIG. 4 illustrates exemplary B-scan images obtained with a low-cost Line-field OCT system, internal limiting membrane (ILM), and retinal pigment epithelium (RPE) segmentation in accordance with the present invention.

Referring to FIG. 4, FIG. 4 provides an exemplary set of B-scan images 400 obtained with a low-cost Line-field OCT system, highlighting ILM and RPE segmentation. In various embodiments, the set of B-scans includes B-scans 410, 420, 430, 440, 450, and 460.

In an implementation, a commercial OCT device may provide a macular thickness analysis tool that operates on a single OCT scan. That is, macular thickness analysis is usually based on a single macular thickness map that is generated by a single (high-quality) OCT cube scan, such as may be provided by a high-quality, professional-grade OCT system. However, a single low-quality scan (such as produced by a low-cost line-field OCT system) may not be of good enough quality to reliably generate a macular thickness map.

In various exemplary embodiments, the present invention introduces a process for robust macular thickness analysis that may be suitable for use with a low-cost line-field OCT, but as it should also be understood in the art, the present invention may optionally be used or contemplated for use with other (e.g., higher cost, higher quality) OCT systems. An embodiment of the present invention may provide a process that uses multiple scans and then combines the macular thickness maps generated by the individual scans. This process may improve the accuracy as well as repeatability and reproducibility of macular thickness analysis. Embodiments of the present invention may make use of the following two novel algorithms: OCT signal quality map; and Segmentation Confident map, the implementation of both algorithms will be in more detail in the present disclosure. While prior approaches may use a single scan to generate a macular thickness map and analysis, the present invention implements a process that uses multiple (e.g., cube) scans, and then combines multiple macular thickness maps to create a single high-quality macular thickness map. Hereinbelow, a method for combining these maps is described.

Figure 5:
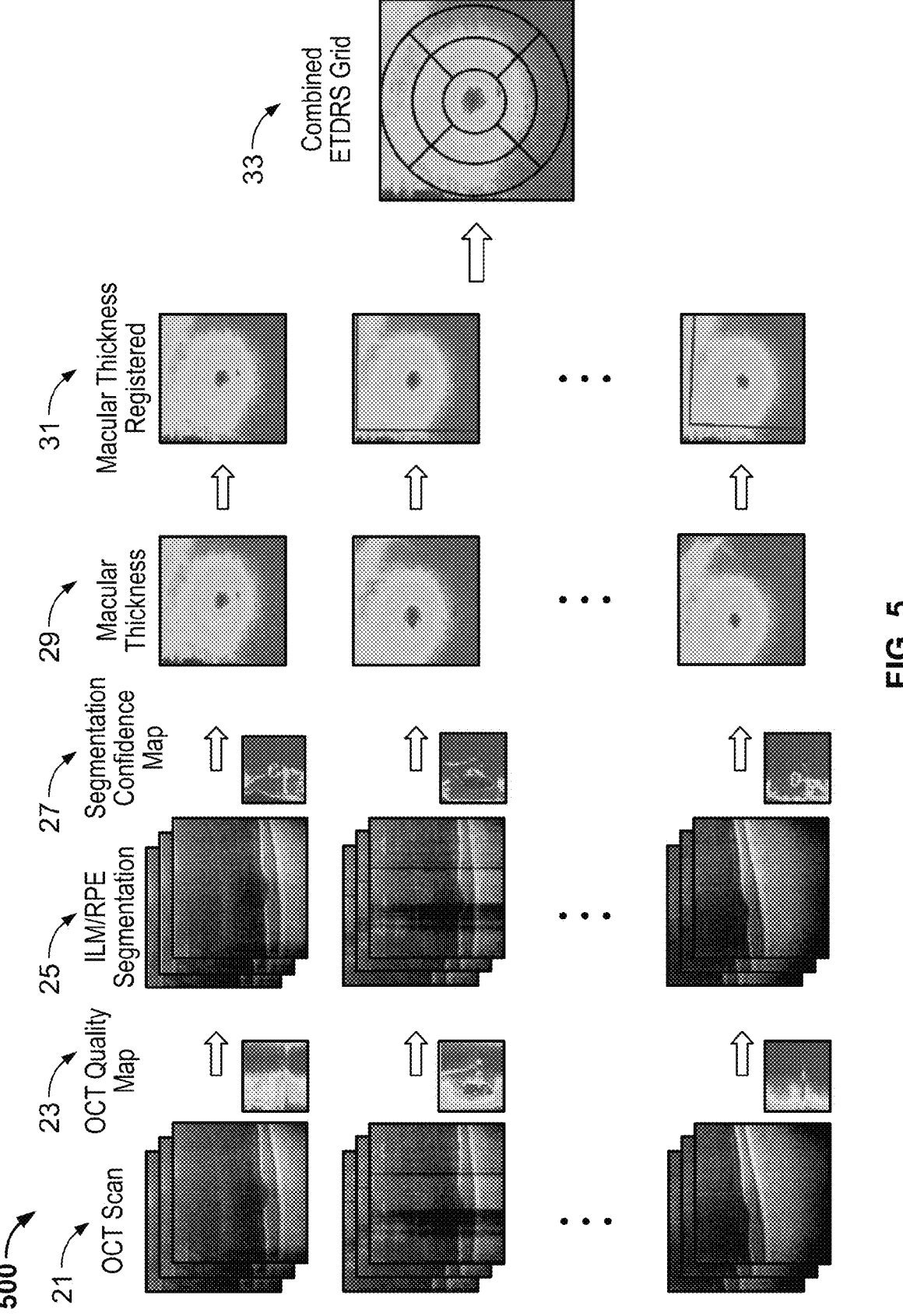
FIG. 5 illustrates a series of images showing a method for robust macular thickness analysis using a low-cost line-field OCT in accordance with the present invention.

Referring to FIG. 5, FIG. 5 shows a method 500 for robust macular thickness analysis using a low-cost line-field OCT in accord with the present invention. In FIG. 5, there is illustrated a process for creating a thickness map of the retinal layers of an eye in accordance with the present invention is shown. This may include the steps of collecting multiple OCT scans (Step 21) (e.g., volume scans or C-scan of the eye, which may be comprised of multiple B-scans each). For each of the OCT (volume) scans, one may generate an OCT quality map (Step 23) based on the quality of the OCT scan(s), as is known in the art. At least two retinal layers are segmented, wherein a thickness map is desired between these two segmented retinal layers. That is, a first target retinal layer (boundary/surface) and a second target layer lower (boundary/surface) are segmented, where one of the first and second retinal layers is higher than the other within the OCT scan (e.g., within the retina). In the present example, the ILM and RPE retinal layers are segmented (Step 25). A segmentation confidence map (or thickness confidence map) (Step 27) is generated using any of the multiple methods known in the art. A respective, preliminary thickness map (e.g., macular thickness map in the present example) (Step 29) is generated based on the first and second target layers (e.g., between the ILM and RPE retinal layers). If not already created, a respective thickness confidence map may be defined/created at this time for each preliminary thickness map. The thus-created preliminary thickness maps (e.g., respective macular thickness maps) are then registered with each other (Step 31). For example, the thickness map of the highest overall quality, e.g., as determined from the respective thickness quality maps, may be selected as a reference thickness map, and the remaining thickness maps registered to this reference thickness map. A combined thickness map (e.g., an Early Treatment Diabetic Retinopathy Study (ETDRS)) (Step 33) may be defined from the multiple thickness maps. For example, poor scan quality sections/parts may be removed from each of the first and second segmented layers based on their respective OCT quality maps (e.g., remove sections whose quality is less than a predetermined/predefined minimum quality threshold), such that those portions are absent from their respective thickness maps. Alternatively, or in addition, regions of low quality (e.g., below a predefined threshold) within the reference thickness map may be identified and replaced by corresponding regions from a combination of one or more other registered quality maps of higher quality. For example, a low-quality region of the reference thickness map may be selectively combined, or replaced, with a corresponding region of the highest quality from among the other registered thickness maps. Alternatively, or in a combination, the low-quality region (or another low-quality region) of the reference thickness map may be combined or replaced by a weighted average of corresponding regions from the other registered thickness maps, where the weights may be based on each respective thickness map's segmentation/thickness confidence map.

The present approach acquires multiple (cube/slab/volume) OCT scans, generates a respective (e.g., macular) thickness map for each scan, and combines the macular thickness maps generated by the individual scans. The process of this approach may be defined as follows: For each cube scan:

1) Determine if the (cube) scan is qualified for further processing such as segmentation. This may be determined from its corresponding OCT quality map.
2) Segment the retina (ILM and RPE) if the scan is qualified
3) Compute a segmentation confidence map. It is understood that one may equivalently compute a thickness quality map. For example, a thickness map may be defined as the separation between the segmented layers, and the segmented layer's respective segmentation confidence/quality thereby defining/determining the quality/confidence of the determined thickness.

4) Generate macular thickness maps using ILM and RPE segmentation. Using all the generated macular thickness maps:
5) designate one of the macular thickness maps as a reference macular thickness map, and register the other macular thickness maps to the reference macular thickness map.
6) Transform the segmentation confidence maps to their corresponding, registered thickness maps.
7) Combine registered macular thickness maps. The combined macular thickness map can be generated by a weighted average of the individual registered thickness maps. The transformed segmentation confidence maps can be used as weight maps.

Alternatively, an Early Treatment Diabetic Retinopathy Study (ETDRS) grid of individual maps can be combined. In this case, for corresponding ETDRS grid sectors among the individual maps, the ETDRS grid sector value with the highest average segmentation confidence within the sector is used/reported. Other known map fusion approaches may also be used.

In various embodiments, several different algorithms may be used in the implementation of the process described in the present invention that includes:

1) OCT signal quality
2) ILM/RPE segmentation
3) Segmentation confidence
4) Macular thickness
5) Macular thickness registration
6) Combined macular thickness map

OCT Signal Quality Algorithm

Figures 6, 7:
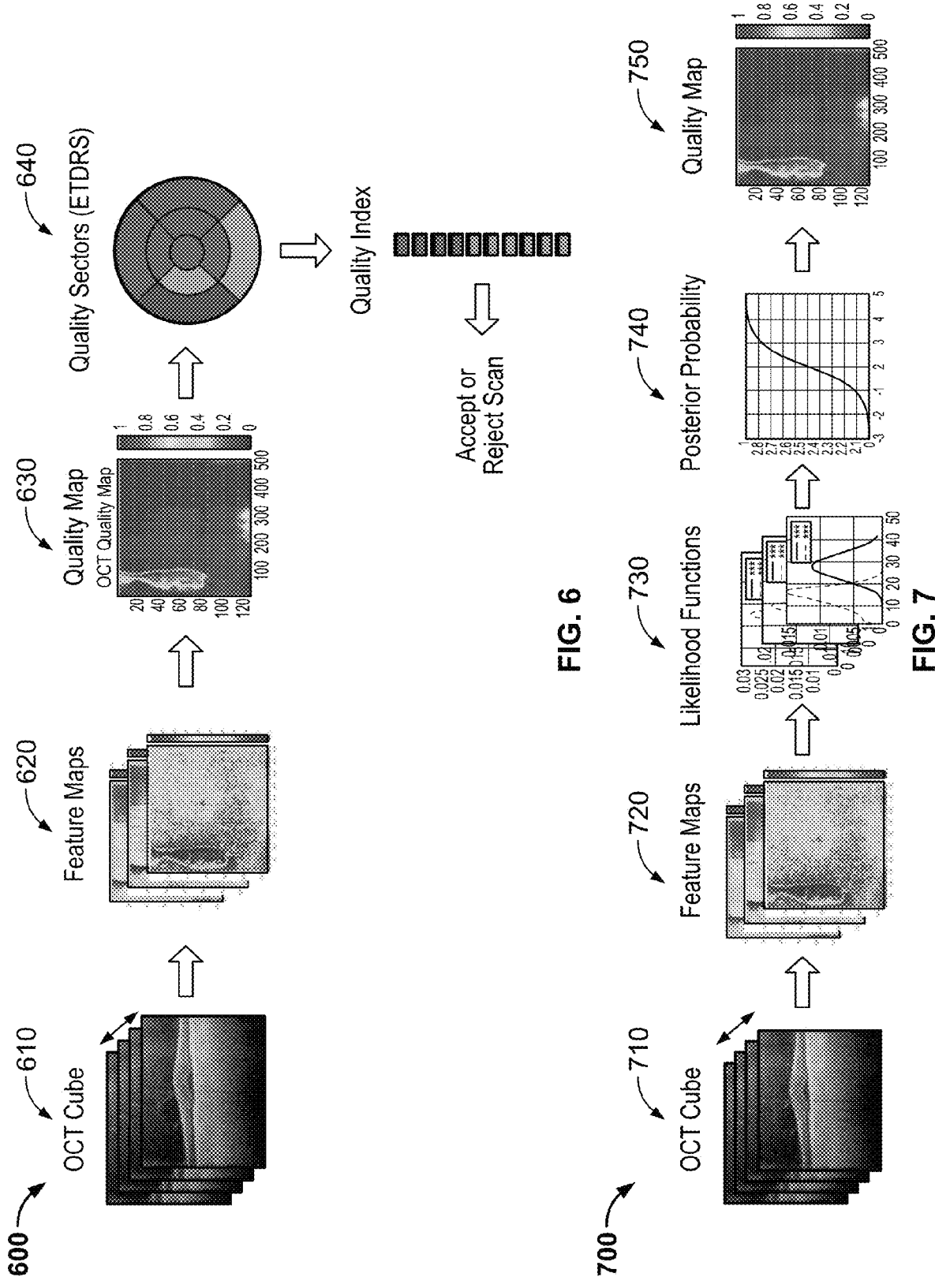
FIG. 6 illustrates a series of diagrams of the mapping of an OCT volume to some intermediate processing steps in accordance with the present invention.
FIG. 7 illustrates a series of diagrams of an example of feature maps being combined into (to define) a single quality map in accordance with the present invention.

Referring to FIG. 6, FIG. 6 illustrates the mapping 600 of an OCT volume to some intermediate processing steps, as discussed above. As shown, an OCT cube scan may be comprised of multiple B-scans. The mapping 600 includes configuring from an OCT cube 610, feature maps 620, quality map 630, quality sectors 640, and a quality index 650 for acceptance or rejection of a scan. Respective feature maps may be defined/generated for each B-scan, and an OCT quality map thereby is defined. In various embodiments, one may then define a quality sector map (ETDRS), and use a quality index to determine whether to accept or reject an individual scan, or individual sectors.

Feature Maps

The quality of an A-scan or a group of neighboring A-scans can be measured by a set of metrics. Three metrics, which may include signal strength (mean intensity), signal-to-background ratio (SBR), and signal contrast, can be used to create three feature maps for all A-scans in an OCT volume (scan). The pixel dimensions of a feature map are the same as the lateral pixel dimensions of the OCT volume. For instance, the three metrics can be used during alignment by calculating a quality score using one or more B-scans.

Note that other metrics such as entropy or higher statistical moments could be considered to create additional feature maps. However, additional metrics might be redundant or create more computational complexity, which may not be desirable.

Quality Map

Referring to FIG. 7, FIG. 7 provides an example of feature map 700 being combined into (to define) a single quality map. In various exemplary embodiments, an OCT cube 710 is used to configure feature maps 720 to which a likelihood function 730 is applied, and a posterior probability function 740 to a subsequent quality map 750. The quality map 750 indicates the local quality of an OCT scan. Using this map helps the operator or automated algorithm to determine if a volume scan is of sufficient quality to qualify for further analysis. Another application of quality map(s) would be to exclude scan areas with poor quality from any type of quantification determination/judgment. Quality map 750 can be created using Bayesian inference, as shown in FIG. 7. For Bayesian inference, likelihood functions for good and poor feature map data are required. Likelihood functions are determined by grouping the feature map data into poor and good-quality groups.

Quality Sectors

The local values of a quality map 750 can be averaged and reduced in quality sectors. The sectors with high scores can be used for a quantification report on the screen.

Quality Index

Overall OCT cube/volume 710 quality can be summarized as a quality index. The quality index can be calculated using the feature maps directly or using the quality map/sectors.

Segmentation and Segmentation Confidence Map

ILM/RPE (or other first layer/second layer) segmentation can be segmented using any automatic retinal segmentation method/algorithm known in the art. ILM and RPE segmentations are based on cost images that are generated from multiple processed OCT images. The segmentation confidence is calculated as the minimum of ILM and RPE segmentation confidences for each lateral location of the scan. ILM and RPE segmentation confidence maps are generated from the value of the ILM and RPE cost images at each segmentation point.

Figures 8A, 8B:
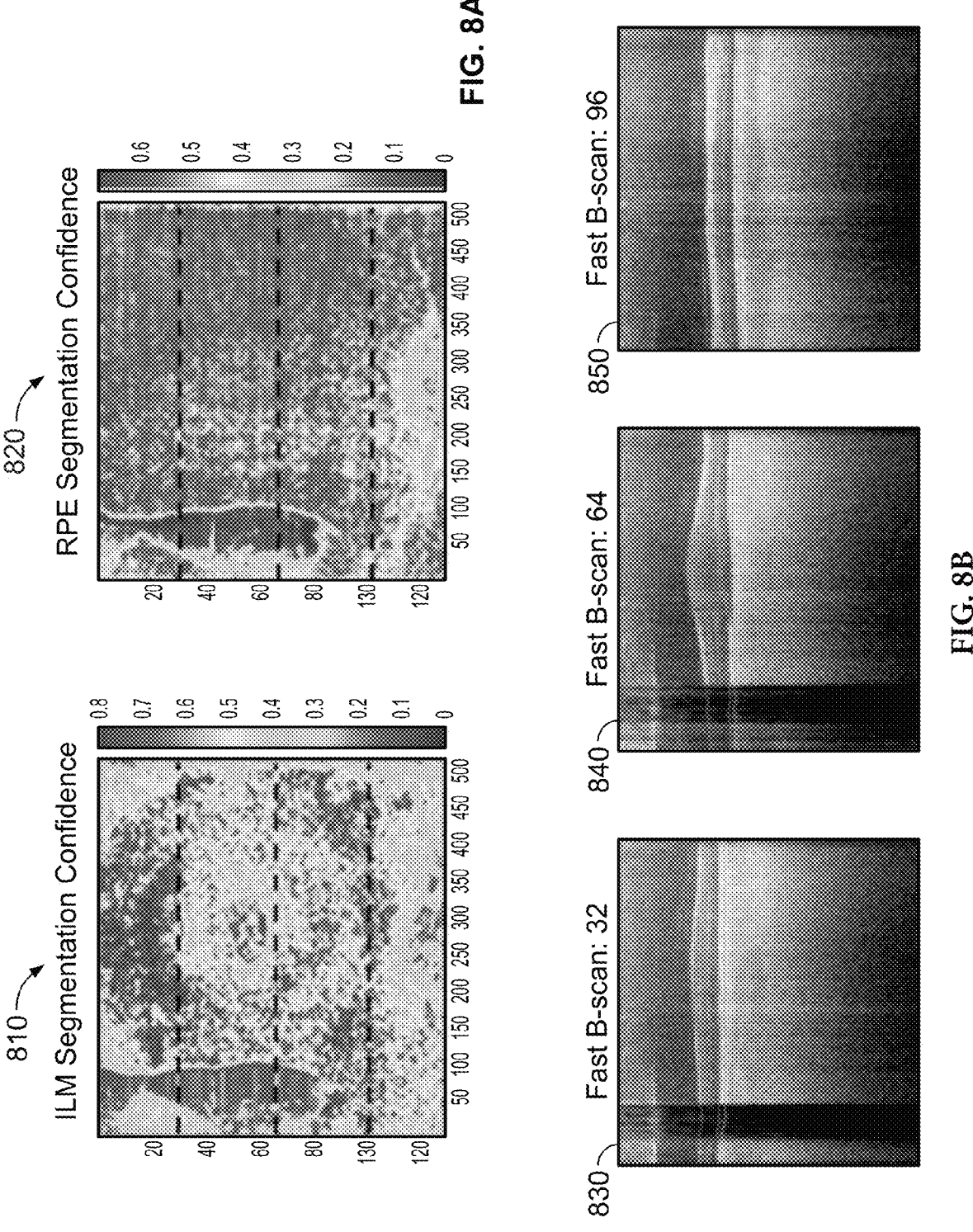
FIG. 8A illustrates exemplary scans that show the segmentation confidence maps for an ILM and RPE segmentation from an exemplary OCT volume scan in accordance with the present invention.
FIG. 8B illustrates exemplary scans that show three B-scans of the same cube scan as FIG. 8A in accordance with various embodiments.

Referring to FIGS. 8A and 8B, FIG. 8A shows the segmentation confidence maps for an ILM segmentation 810 and RPE segmentation 820 from an exemplary OCT volume scan and FIG. 8B shows three B-scans 830, 840, and 850 (as labeled in accordance with FIG. 8A) of the same cube scan. The bluish area (areas with confidence below about 3.25 or below 2.5) in ILM and RPE segmentation confidence maps correspond to the segmentation region in B-scans with low confidence.

Figures 9, 10:
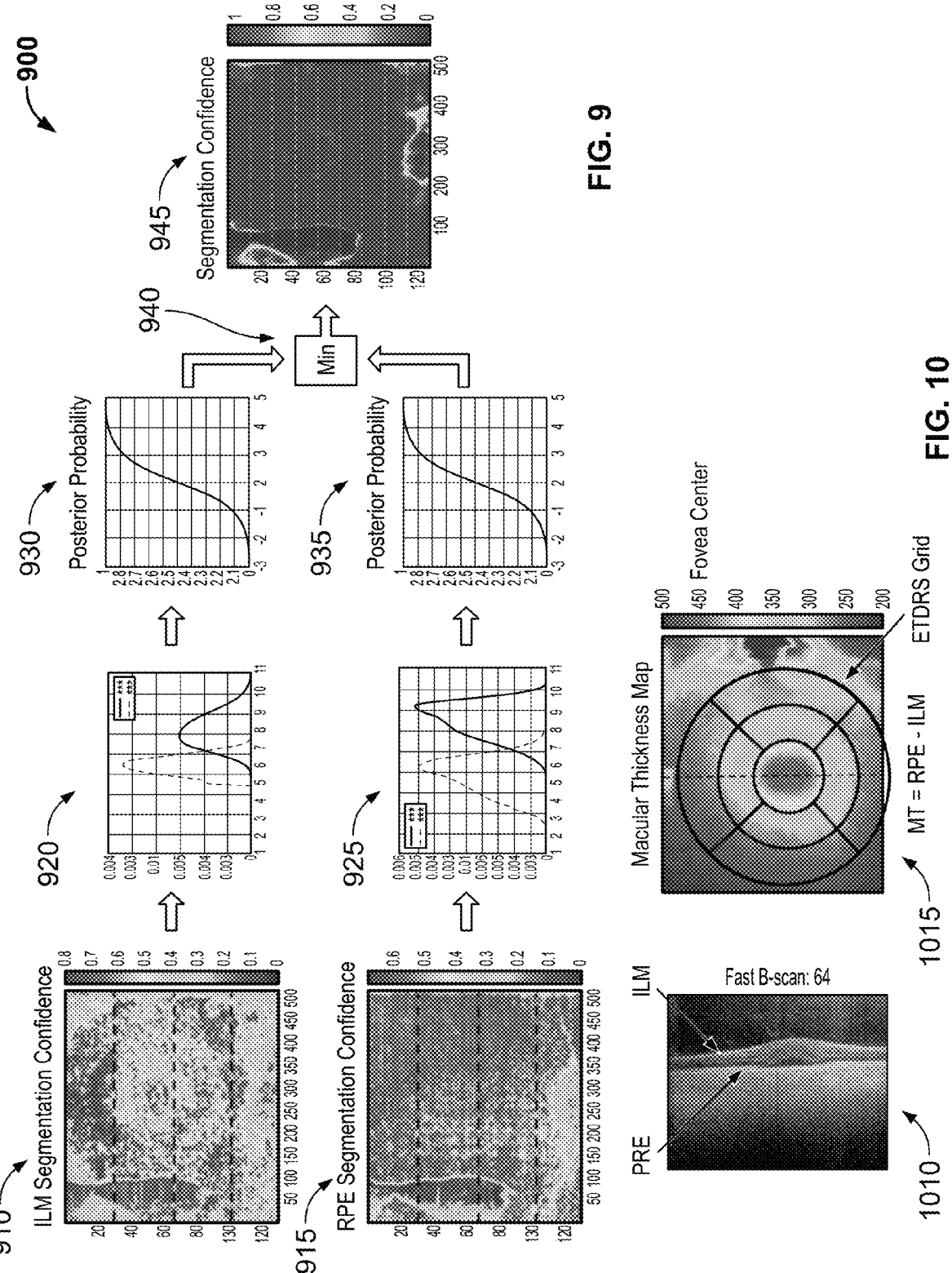
FIG. 9 illustrates an exemplary set of images of the generation of a segmentation confidence map by combining ILM and RPE segmentation confidence maps in accordance with the present invention.
FIG. 10 illustrates exemplary images that show the thickness map of a central serous retinopathy (CSR) case in accordance with the present invention.

Referring to FIG. 9, in diagram 900 a segmentation confidence map 945 may be generated by combining the ILM segmentation confidence map 910 and RPE segmentation confidence map 915, as illustrated in FIG. 9. As shown in FIG. 9, the segmentation confidence map 945 can be created using Bayesian inference. For Bayesian inference, likelihood functions 920, and 925 for high and low ILM and RPE confidence map data are required. Likelihood functions may be determined by using high and low ILM and RPE confidence map data. Also, posterior probability functions 930, and 935 are applied for high and low ILM and RPE confidence map data with a min function 940 application to generate the segmentation confidence map 945.

Macular Thickness Map and Registration

Referring to FIG. 10, various exemplary macular thickness maps 1010 and 1015 are generated based on the difference between ILM and RPE in the axial direction. FIG. 10 shows the thickness map of a central serous retinopathy (CSR) case.

In FIG. 10, Prior to combining the macular thickness maps, the thickness maps need to be registered first. Various registration algorithms can be used to register the OCT data or maps directly. Examples of suitable registration algorithms are provided in Andrew Lang, et al., "Combined Registration and Motion Correction of Longitudinal Retinal OCT Data", *Proc SPIE Int Soc Opt Eng.* 2016 Feb. 27; 9784, and in Jing Wu, et al., "Stable Registration of Pathological 3D-OCT Scans Using Retinal Vessels," *Proceedings of the Ophthalmic Medical Image Analysis International Workshop, Sep.* 14, 2014, both of which are herein incorporated in their entirety by reference.

Figure 11:
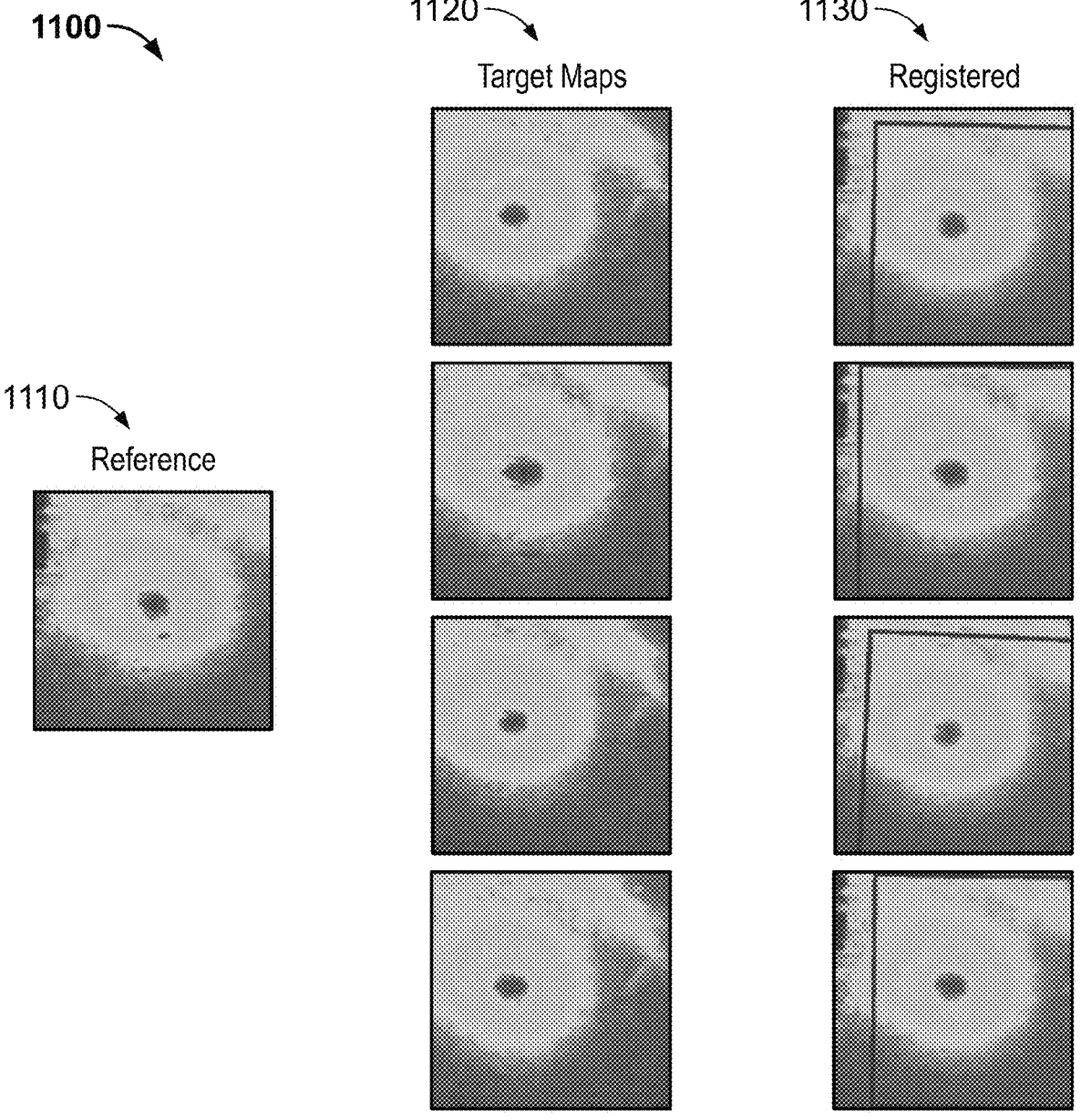
FIG. 11 illustrates exemplary images of the registration of four macular thickness maps to a reference thickness map of the scans from the same visit in accordance with the present invention.

Referring to FIG. 11, FIG. 11 shows diagram 1100 of the registration of four macular thickness maps 1130 to a reference thickness map 1110 of the scan of four target maps 1120 from the same visit.

Combined Macular Thickness Map

One way to generate a combined macular thickness is based on a weighted average of registered individual macular thicknesses at each lateral position. The weight values may be the corresponding lateral position of each transformed segmentation confidence map.

Alternatively, ETDRS grids of individual maps can be combined. The grid sector value with the highest average segmentation confidence within the sector is reported. Other map fusion techniques could be considered.

Hereinafter is provided a description of various hardware and architectures suitable for the present invention.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photosensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image segments that may be reconstructed, e.g., montaged, to create a composite image of the desired FOV. The scan beam could be a point, a line, or a two-dimensional area such as a slit or broad line. Examples of fundus imagers are provided in U.S. Pat. Nos. 8,967,806 and 8,998,411.

Figure 12:
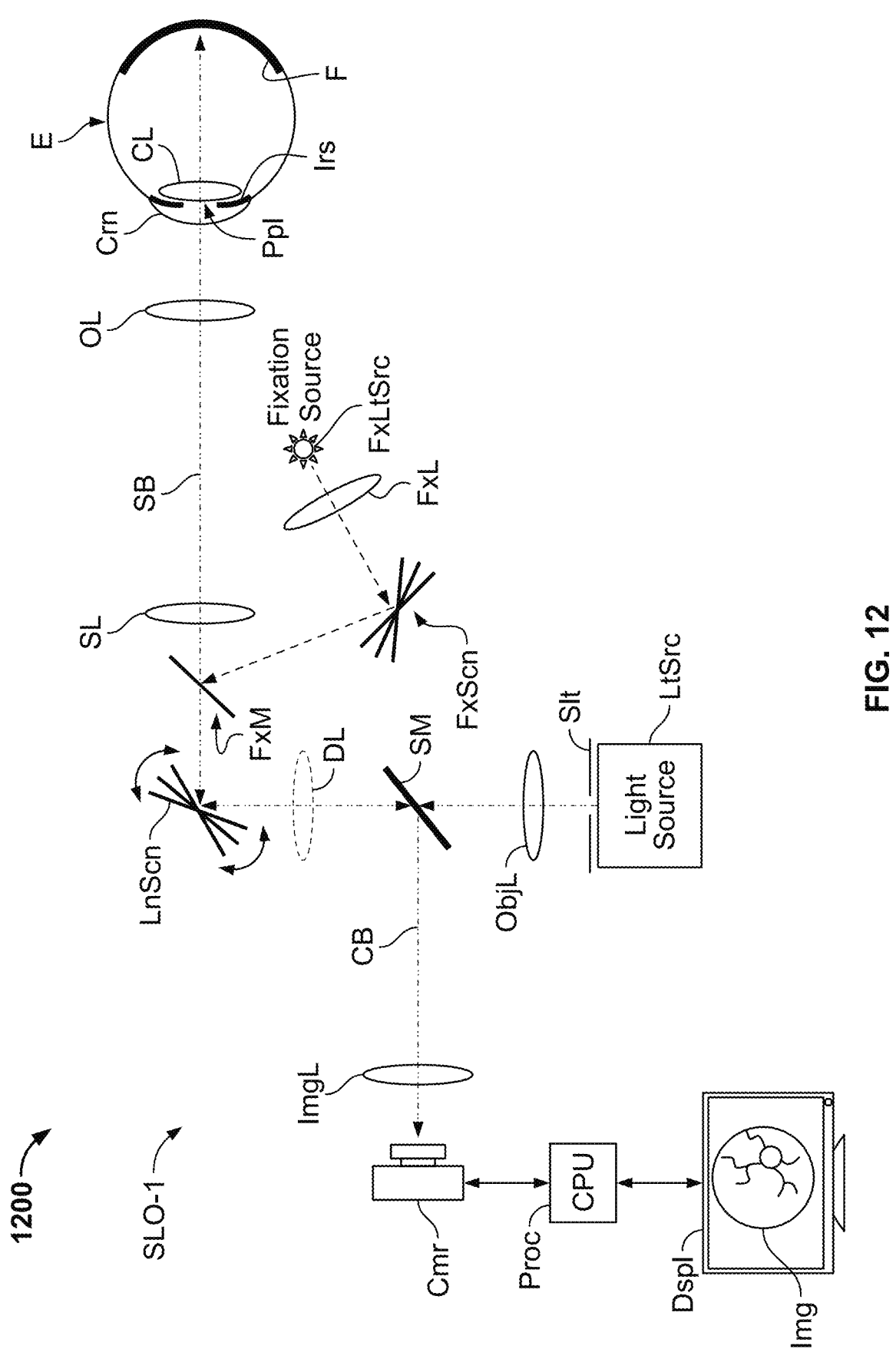
FIG. 12 illustrates a diagram of an example of a slit scanning ophthalmic system for imaging a fundus in accordance with the present invention.

Referring to FIG. 12, FIG. 12 illustrates diagram 1200 an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Cm, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/systems. The light from slit Slt passes through a pupil-splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil-splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case, a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles) and produces a scanning line beam SB with a substantially flat surface focal plane (e.g., a collimated light path). Ophthalmic lens OL may then focus the scanning line beam SB onto an object to be imaged. In the present example, the ophthalmic lens OL focuses the scanning line beam SB onto the fundus F (or retina) of eye E to image the fundus. In this manner, scanning line beam SB creates a traversing scan line that travels across the fundus F.

In various exemplary embodiments, one possible configuration for these optics is a Kepler-type telescope wherein the distance between the two lenses is selected to create an approximately telecentric intermediate fundus image (4-f configuration). The ophthalmic lens OL could be a single lens, an achromatic lens, or an arrangement of different lenses. All lenses could be refractive, diffractive, reflective, or hybrid as known to one skilled in the art. The focal length(s) of the ophthalmic lens OL, scan lens SL, and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with other imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

In various exemplary embodiments, the scanning line beam SB passes through the pupil Ppl of the eye E and is directed towards the retinal, or fundus, surface F. The scanner LnScn1 adjusts the location of the light on the retina, or fundus, F such that a range of transverse locations on the eye E is illuminated. Reflected or scattered light (or emitted light in the case of fluorescence imaging) is directed back along a similar path as the illumination to define a collection beam CB on a detection path to camera Cmr.

In various exemplary embodiments, in the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., canceling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr.

As is the case for objective lens ObjL, imaging lens ImgL may be any type of lens known in the art (e.g., refractive, diffractive, reflective, or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system illustrated in FIG. 17). Thus, the collection beam (returning from all scan positions of the scanning line beam SB) is collected by the camera Cmr, and a full-frame image Img may be constructed from a composite of the individually captured collection beams, such as by montaging. However, other scanning configurations are also contemplated, including ones where the illumination beam is scanned across the eye E and the collection beam is scanned across a photosensor array of the camera. PCT Publication WO 2012/059236 and U.S. Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dsp1, both of which can be part of the imaging system, or maybe part of separate, dedicated processing and/or displaying unit(s), such as a computer system wherein data is passed from the camera Cmr to the computer system over a cable or computer network including wireless networks. The display and processor can be an all-in-one unit. The display can be a traditional electronic display/screen or of the touch screen type and can include a user interface for displaying information to and receiving information from an instrument operator or user. The user can interact with the display using any type of user input device as known in the art including, but not limited to, a mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged.

Referring to FIG. 12, an exemplary embodiment of an internal fixation target is shown in FIG. 12. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is positioned such that it is located at the pupil plane of the system so that the light pattern on the retina/fundus can be moved depending on the desired fixation location.

Slit-scanning ophthalmoscope systems are capable of operating in different imaging modes depending on the light source and wavelength-selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Additionally, the light at specific frequencies (e.g., individual-colored LEDs or lasers) can be used to excite different fluorophores in the eye (e.g., auto-fluorescence) and the resulting fluorescence can be detected by filtering out the excitation wavelength.

The fundus imaging system can also provide an infrared reflectance image, such as by using an infrared laser (or other infrared light sources). The infrared (IR) mode is advantageous in that the eye is not sensitive to the IR wavelengths. This may permit a user to continuously take images without disturbing the eye (e.g., in a preview/alignment mode) to aid the user during the alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream. For example, in FA (and/or ICG) a series of time-lapse images may be captured after injecting a light-reactive dye (e.g., fluorescent dye) into a subject's bloodstream. It is noted that care must be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye.

Optical Coherence Tomography Imaging System

Generally, optical coherence tomography (OCT) uses low-coherence light to produce two-dimensional (2D) and three-dimensional (3D) internal views of biological tissue. OCT enables in vivo imaging of retinal structures. OCT angiography (OCTA) produces flow information, such as vascular flow from within the retina. Examples of OCT systems are provided in U.S. Pat. Nos. 6,741,359 and 9,706,915, and examples of an OCTA system may be found in U.S. Pat. Nos. 9,700,206 and 9,759,544, all of which are herein incorporated in their entirety by reference. An exemplary OCT/OCTA system is provided herein.

Figure 13:
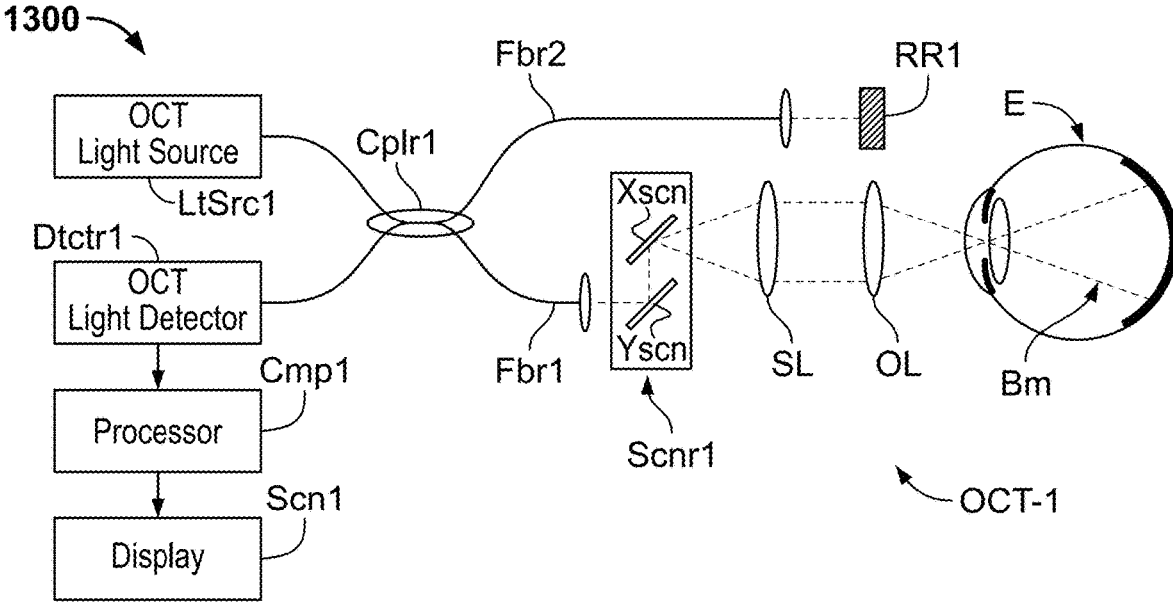
FIG. 13 illustrates a diagram of a generalized frequency domain optical coherence tomography system used to collect 3D image data of the eye suitable for use with the present invention.

Referring to FIG. 13, FIG. 13 illustrates diagram 1300 of a generalized frequency domain optical coherence tomography (FD-OCT) system used to collect 3D image data of the eye suitable for use with the present invention. An FD-OCT system OCT_1 includes a light source, LtSrc1. Typical light sources include but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 may, for example, be a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally over the region of the sample to be imaged. The light beam from scanner Scnr1 may pass through a scan lens SL and an ophthalmic lens OL and be focused onto the sample E being imaged. The scan lens SL may receive the beam of light from the scanner Scnr1 at multiple incident angles and produce substantially collimated light, and the ophthalmic lens OL may then focus onto the sample. The present example illustrates a scan beam that needs to be scanned in two lateral directions (e.g., in x and y directions on a Cartesian plane) to scan a desired field of view (FOV). An example of this would be a point-field OCT, which uses a point-field beam to scan across a sample. Consequently, scanner Scnr1 is illustratively shown to include two sub-scanner: a first sub-scanner Xscn for scanning the point-field beam across the sample in a first direction (e.g., a horizontal x-direction); and a second sub-scanner Yscn for scanning the point-field beam on the sample in traversing second direction (e.g., a vertical y-direction). If the scan beam were a line-field beam (e.g., a line-field OCT), which may sample an entire line portion of the sample at a time, then only one scanner may be needed to scan the line-field beam across the sample to span the desired FOV. If the scan beam were a full-field beam (e.g., a full-field OCT), no scanner may be needed, and the full-field light beam may be applied across the entire, desired FOV at once.

Irrespective of the type of beam used, light scattered from the sample (e.g., sample light) is collected. In the present example, scattered light returning from the sample is collected into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, for example, in a fiber coupler Cplr1, to form light interference in an OCT light detector Dtctr1 (e.g., photodetector array, digital camera, etc.).

Figure 17:
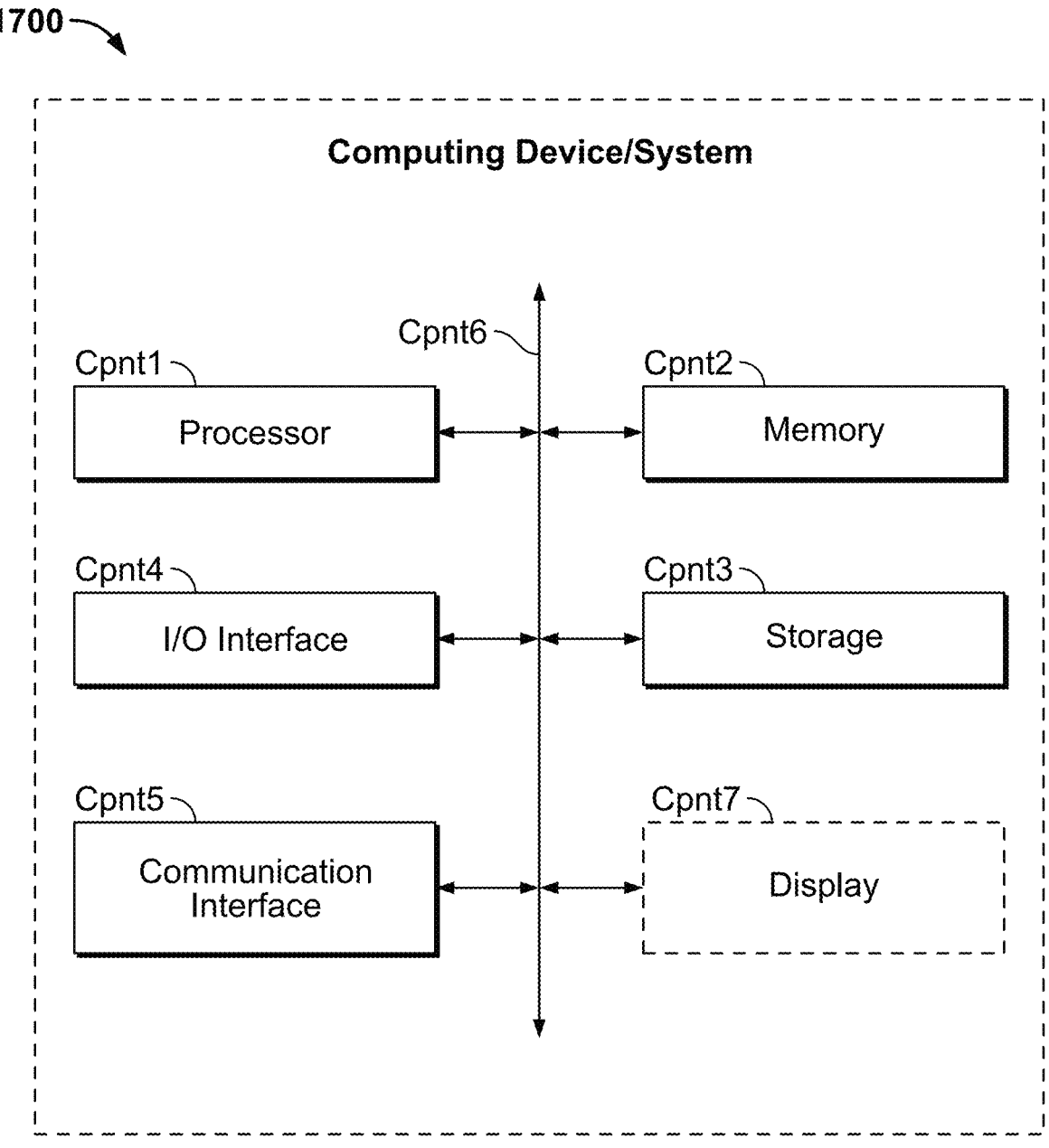
FIG. 17 illustrates a diagram of an example computer system (or computing device or the computer) in accordance with the present invention.

Although a single fiber port is shown going to the detector Dtctr1, those skilled in the art will recognize that various designs of interferometers can be used for balanced or unbalanced detection of the interference signal. The output from the detector Dtctr1 is supplied to a processor (e.g., internal or external computing device) Cmp1 that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument, or functions may be offloaded onto (e.g., performed on) an external processor (e.g., an external computing device), to which the collected data may be transferred. An example of a computing device (or computer system) is shown in FIG. 17. This unit could be dedicated to data processing or perform other tasks which are quite general and not dedicated to the OCT device. The processor (computing device) Cmp1 may include, for example, a field-programmable gate array (FPGA), a digital signal processor (DSP), an application-specific integrated circuit (ASIC), a graphics processing unit (GPU), a system-on-chip (SoC), a central processing unit (CPU), a general purpose graphics processing unit (GPGPU), or a combination thereof, that may perform some, or the entire, processing steps in a serial and/or parallelized fashion with one or more host processors and/or one or more external computing devices.

The sample and reference arms in the interferometer could consist of bulk-optics, fiber-optics, or hybrid bulk-optic systems and could have different architectures such as Michelson, Mach-Zehnder, or common-path-based designs as would be known by those skilled in the art. Light beam as used herein should be interpreted as any carefully directed light path. Instead of mechanically scanning the beam, a field of light can illuminate a one or two-dimensional area of the retina to generate the OCT data (see, for example, U.S. Pat. No. 9,332,902; D. Hillmann et al, "Holoscopy—Holographic Optical Coherence Tomography," *Optics Letters,* 36(13): 2390 2011; Y. Nakamura, et al, "High-Speed Three Dimensional Human Retinal Imaging by Line Field Spectral Domain Optical Coherence Tomography," *Optics Express,* 15(12):7103 2007; Blazkiewicz et al, "Signal-To-Noise Ratio Study of Full-Field Fourier-Domain Optical Coherence Tomography," *Applied Optics,* 44(36): 7722 (2005)). In time-domain systems, the reference arm needs to have a tunable optical delay to generate interference. Balanced detection systems are typically used in TD-OCT and SS- OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram results in a complex-valued OCT signal output $Aj(z)=|Aj|e i\varphi$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex-valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas the slow axis refers to the axis along which multiple B-scans are collected. The term "cluster scan" may refer to a single unit or block of data generated by repeated acquisitions at the same (or substantially the same) location (or region) to analyze motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meet predefined criteria may be identified as blood flow.

A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross-sectional image that includes the z-dimension. An example OCT B-scan image of a normal retina of a human eye is illustrated in FIG. 14. An OCT B-scan of the retinal provides a view of the structure 1420 of retinal tissue. For illustration purposes, FIG. 14 identifies various canonical retinal layers and layer boundaries. The identified retinal boundary layers 1410 include (from top to bottom): the inner limiting membrane (ILM) Lyer1, the retinal nerve fiber layer (RNFL or NFL) Layr2, the ganglion cell layer (GCL) Layr3, the inner plexiform layer (IPL) Layr4, the inner nuclear layer (INL) Layr5, the outer plexiform layer (OPL) Layr6, the outer nuclear layer (ONL) Layr7, the junction between the outer segments (OS) and inner segments (IS) (indicated by reference character Layr8) of the photoreceptors, the external or outer limiting membrane (ELM or OLM) Layr9, the retinal pigment epithelium (RPE) Layr10, and the Bruch's membrane (BM) Layr11.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2012/

0307014, 2010/0027857; and U.S. Pat. Nos. 8,433,393, 6,549,801, and 7,359,062 all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en-face vasculature image is an image displaying a motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 15:
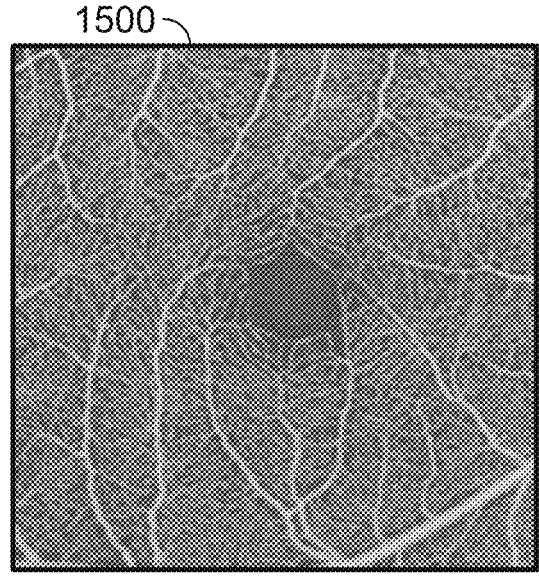
FIG. 15 illustrates an exemplary image that shows an example of an en-face vasculature image in accordance with the present invention.
Figure 16:
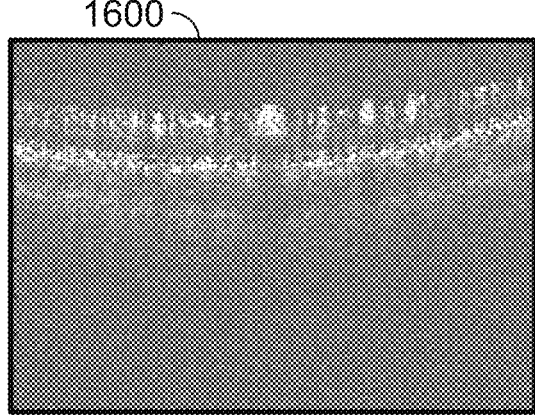
FIG. 16 illustrates an exemplary image that shows an exemplary B-scan of a vasculature (OCTA) image in accordance with the present invention.

Referring to FIG. 15, FIG. 15 shows an exemplary B-scan 1500 of an example of an en-face vasculature image. After processing the data to highlight motion contrast using any of the motion contrast techniques known in the art, a range of pixels corresponding to a given tissue depth from the surface of the internal limiting membrane (ILM) in the retina, may be summed to generate the en face (e.g., frontal view) image of the vasculature. Referring to FIG. 16, FIG. 16 shows an exemplary B-scan 1600 of a vasculature (OCTA) image. As illustrated, structural information may not be well-defined since blood flow may traverse multiple retinal layers making them less defined than in a structural OCT B-scan, as shown in FIG. 14. Nonetheless, OCTA provides a non-invasive technique for imaging the microvasculature of the retina and the choroid, which may be critical to diagnosing and/or monitoring various pathologies. For example, OCTA may be used to identify diabetic retinopathy by identifying microaneurysms, and neovascular complexes, and quantifying foveal avascular zone and nonperfused areas. Moreover, OCTA has been shown to be in good agreement with fluorescein angiography (FA), a more traditional, but evasive, technique requiring the injection of a dye to observe vascular flow in the retina. Additionally, in dry age-related macular degeneration, OCTA has been used to monitor a general decrease in choriocapillaris flow. Similarly, in wet age-related macular degeneration, OCTA can provide a qualitative and quantitative analysis of choroidal neovascular membranes. OCTA has also been used to study vascular occlusions, e.g., evaluation of nonperfused areas and the integrity of superficial and deep plexus.

Computing Device/System

Referring to FIG. 17, FIG. 17 illustrates diagram 1700 of an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on the graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, and one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers and may include one or more arithmetic logic units (ALUs). Processor Cpnt1 may be a multi-core processor or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or another source (such as another computer system) to memory Cpnt2. Processor Cpnt1 may load the instructions and data from memory Cpnt2 to one or more internal registers or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2, or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management units (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, a magneto-optical disc, magnetic tape, Universal Serial Bus (USB)-accessible drive, or other types of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other types of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. Furthermore, the connecting lines shown in the various figures contained herein are intended to represent various functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Furthermore, no element, component, or method step in the present disclosure is intended to be dedicated to the public regardless of whether the element, component, or method step is explicitly recited in the claims. No claim element herein is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications, and variations as may fall within the spirit and scope of the appended claims.

What is claimed is:

1. A method of creating a composite retinal thickness map of an eye, comprising:
   collecting, by an optical coherence tomography (OCT) device, a set of a plurality of optical coherence tomography (OCT) volume scans of the eye wherein at least one set of the plurality of OCT volume scans are collected by the OCT device by:
      segmenting a target upper retinal layer and a target lower retinal layer which is lower than the target upper retinal layer within an OCT volume scan;
      determining a thickness map of a candidate between the upper retinal layer and lower retinal layer, and a confidence map associated with the thickness map;

23 selecting at least one thickness map as a reference thickness map,
wherein the selected reference thickness map is the thickness map that has a highest confidence measure based on the confidence map;
registering remaining at least one thickness map to the reference thickness map; and
selectively combining a region of the thickness map with a corresponding region of the reference thickness map to define a composite retinal thickness map.

2. The method of claim 1, wherein selectively combining the region of the thickness map with the corresponding region of the reference thickness map comprises:
identifying a region of low quality within the reference thickness map based on the confidence map; and
replacing the region of low quality with a combination of the corresponding region from an alternate thickness map.

3. The method of claim 2, wherein the corresponding region is of higher quality than a low-quality region based on the confidence map.

4. The method of claim 1, wherein the confidence map is based on at least one of a corresponding OCT signal quality map or a segmentation confidence map.

5. The method of claim 1, wherein the target upper retinal layer is an internal limiting membrane (ILM) layer, and the target lower retinal layer is lower than a retinal pigment epithelium (RPE) layer.

6. The method of claim 1, wherein at least one set of the plurality of volume scans is associated with a corresponding segmentation confidence map wherein the at least one thickness map is registered to the reference thickness map wherein registration includes transforming the corresponding segmentation confidence map based on the at least one thickness map.

7. The method of claim 6, wherein selection of a corresponding region from other thickness maps is enabled by a combination of a weighted average of at least one individual registered map, and wherein a set of weights for the weighted average is based on a corresponding confidence map.

8. The method of claim 1, wherein at least one region of the thickness map of the candidate is selected for processing with information associated with an Early Treatment Diabetic Retinopathy Study (ETDRS).

9. A method of creating a composite retinal thickness map of an eye, comprising:
collecting, by an optical coherence tomography (OCT) device, a set of a plurality of optical coherence tomography (OCT) volume scans of the eye wherein at least one set of the plurality of OCT volume scans are collected by the OCT device by:
segmenting a target upper retinal layer and a target lower retinal layer which is lower than the target upper retinal layer within an OCT volume scan;
determining a thickness map of a candidate between the upper retinal layer and lower retinal layer, and a confidence map associated with the thickness map;
selecting at least one thickness map as a reference thickness map;
registering remaining at least one thickness map to the reference thickness map; and
selectively combining a region of the thickness map with a corresponding region of the reference thickness map using a weighted average function to define a composite retinal thickness map,

wherein the weighted average function is based at least on the confidence map of a selected region of the thickness map.

10. A remote self-examination system for creating a composite retinal thickness map of an eye, comprising:
an optical coherence tomography (OCT) device for collecting a set of a plurality of OCT volume scans of the eye;
a computing device disposed in the OCT device to process data of at least one set of the plurality of OCT volume scans wherein the computing device is configured to:
segment a target upper retinal layer and a target lower retinal layer lower than the target upper retinal layer within an OCT volume scan;
determine a thickness map of a candidate between the upper retinal layer and lower retinal layer, and a confidence map associated with the thickness map;
select at least one thickness map as a reference thickness map;
register the thickness map to the reference thickness map;
selectively combine a region of the thickness map with a corresponding region of the reference thickness map to define the composite retinal thickness map;
selectively combine the region of the thickness map with the corresponding region of the reference thickness map by:
identifying regions of low quality within the reference thickness map associated with the confidence map,
wherein the confidence map is based on at least one of a corresponding OCT signal quality map or a segmentation confidence map; and
replacing the identified regions of low quality with a combination of a selected corresponding region from an alternate thickness map; and
apply a weighted average function based at least on the confidence map of a selected region of the thickness map.

11. The system of claim 10, wherein the OCT device further comprises an electronic communication module to transmit a report based on the defined composite retinal thickness map to a remote health care center.

12. The system of claim 10, wherein the computing device is further configured to select the corresponding region that is of higher quality than a low-quality region based on an association of the confidence map to the corresponding region.

13. The system of claim 10, wherein the computing device is further configured to select the reference thickness map comprising the thickness map having a highest confidence measure associated with the confidence map.

14. The system of claim 10, wherein the region from the thickness map is combined with corresponding regions of the reference thickness map by a weighted average.

15. The system of claim 10, wherein the target upper retinal layer is an internal limiting membrane (ILM) layer, and the target lower retinal layer is lower than a retinal pigment epithelium (RPE) layer.

16. The system of claim 10, wherein at least one set of volume scans that have been collected is associated with a corresponding segmentation confidence map, and wherein the register of the thickness map to the reference thickness map comprises transformation of a segment of the confidence map to a corresponding thickness map.

* * * * *